United States Patent
Manley et al.

(10) Patent No.: US 7,666,874 B2
(45) Date of Patent: *Feb. 23, 2010

(54) PYRIMIDYLAMINOBENZAMIDE DERIVATIVES FOR HYPEREOSINOPHILIC SYNDROME

(75) Inventors: Paul W. Manley, Arlesheim (CH); Jürgen Mestan, Denzlingen (DE); Doriano Fabbro, Arlesheim (CH)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/911,562

(22) PCT Filed: May 2, 2006

(86) PCT No.: PCT/EP2006/004084

§ 371 (c)(1),
(2), (4) Date: Oct. 15, 2007

(87) PCT Pub. No.: WO2006/117185

PCT Pub. Date: Nov. 9, 2006

(65) Prior Publication Data

US 2008/0227800 A1  Sep. 18, 2008

Related U.S. Application Data

(60) Provisional application No. 60/676,751, filed on May 2, 2005.

(51) Int. Cl.
*A61K 31/506* (2006.01)
*C07D 401/14* (2006.01)
*A61P 7/00* (2006.01)
*A61P 35/02* (2006.01)

(52) U.S. Cl. ...................... 514/275; 544/333
(58) Field of Classification Search .................. 544/333; 514/275

See application file for complete search history.

(56) References Cited

U.S. PATENT DOCUMENTS 7,169,791 B2 * 1/2007 Breitenstein et al. ........ 514/275

FOREIGN PATENT DOCUMENTS

| WO | 2004/005281 | 1/2004 |
| WO | 2005/039586 | 5/2005 |
| WO | 2005/049032 | 6/2005 |

OTHER PUBLICATIONS

Cross et al., Leukemia, 16, 1207-1212, 2002.*
Piccaluga et al., Expert Opinion in Biological Therapy, 7(10), 1597-1611, 2007.*
Cecil Textbook of Medicine, edited by Bennet, J.C., and Plum F., 20th edition, vol. 1, 1004-1010, 1996.*
Weisberg et al., "Characterization of AMN107, a selective inhibitor of native and mutant Bcr-Abl," Cancer Cell. vol. 7, No. 2, pp. 129-141 (2005).
Giles et al., "A phase IIII study of AMN107, a novel aminopyrimidine inhibitor of bcr-abl, on a continuous daily dosing schedule in adult patients (pts) with imatinib-resistant advanced phase chronic myeloid leukemia (CML) or relapsed/refractory Philadelphia chromosome (Ph plus) acute lymphocytic leukemia (ALL)," Blood, vol. 104, No. 11, Part 1, pp. 10A-11A (2004).
Martinelli et al., "Imatinib mesylate can induce complete molecular remission in FIP1L-PDGFR-a positive idiopathic hypereosinophilic syndrome," Haematologica, vol. 89, No. 2, pp. 236-237 (2004).
Cools et al., "The FLP1L1-PDGFRALPHA Kinase in Hypereosinophilic Syndrome and Chronic Eosinophilic Leukemia," Current Opinion in Hematology, vol. 11, No. 1, p. 51-57, (2004).
Gunby et al., "Sensitivity to imatinib by low frequency of the TEL/PDGFRbeta fusion protein in chronic myelomonocytic leukemia," Haematologica, vol. 88, No. 4, pp. 408-415 (2003).

* cited by examiner

*Primary Examiner*—Venkataraman Balasubramanian
(74) *Attorney, Agent, or Firm*—Matthew Mulkeen

(57) ABSTRACT

The present invention relates to the use of pyrimidylaminobenzamide derivatives for the preparation of a drug for the treatment of FIP1L1-PDGFRα-induced or TEL-PDGFRβ-induced myeloproliferative diseases, especially for the curative and/or prophylactic treatment of hypereosinophilic syndrome and hypereosinophilic syndrome with resistance to imatinib, and to a method of treating hypereosinophilic syndrome, chronic eosinophilic leukemia and hypereosinophilic syndrome with resistance to imatinib, or other diseases associated with FIP1L1-PDGFRα, TEL-PDGFRβ or similar mutations that activate PDGFR.

4 Claims, No Drawings

PYRIMIDYLAMINOBENZAMIDE DERIVATIVES FOR HYPEREOSINOPHILIC SYNDROME

This application claims benefit of U.S. Provisional Application No. 60/676,751, filed May 2, 2005.

SUMMARY OF THE INVENTION

The present invention relates to the use of pyrimidylaminobenzamide derivatives for the treatment of a myeloproliferative disease induced by TEL-PDGFRβ or FIP1L1-PDGFRα, to the manufacture of a medicament for the treatment of a myeloproliferative disease induced by TEL-PDGFRβ or FIP1L1-PDGFRα, and to a method for the treatment of warm-blooded animals, including humans wherein a pyrimidylaminobenzamide derivative is administered to a warm-blooded animal suffering from a myeloproliferative disease induced by TEL-PDGFRβ or FIP1L1-PDGFRα, especially myelomonocytic leukemia, hypereosinophilic syndrome and chronic eosinophilic leukemia; and most especially hypereosinophilic syndrome with resistance to imatinib or myelomonocytic leukemia with resistance to imatinib.

The present invention also relates to a method of treating myelomonocytic leukemia, hypereosinophilic syndrome, chronic eosinophilic leukemia and hypereosinophilic syndrome with resistance to imatinib, or other diseases associated with TEL-PDGFRβ, FIPL1-PDGFRα or similar mutations that activate PDGFR.

BACKGROUND OF THE INVENTION

TEL-PDGFRβ is a fusion kinase that is associated with chronic myelomonocytic leukemia (CMML), a myeloproliferative disorder characterized by abnormal myelopoiesis, eosinophilia, myelofibrosis, and frequent progression to acute myeloid leukemia.

FIP1L1-PDGFRα is a fusion kinase associated with hypereosinophilic syndrome (HES) or chronic eosinophilic leukemia (CEL), a clonal myeloproliferative disorder associated with prominent blood eosinophilia and organ damage.

It has now been shown that pyrimidylaminobenzamide derivatives are active against the clinically relevant fusion kinases TEL-PDGFRβ and FIP1L1-PDGFRα, which are associated with the myeloproliferative diseases CMML and HES, respectively. Furthermore, such pyrimidylaminobenzamide derivatives are effective against myeloproliferative diseases caused by TEL-PDGFRβ and/or FIP1L1-PDGFRα. Pyrimidylaminobenzamide derivatives effectively inhibit growth of Ba/F3 cells transformed by both fusion kinases, and can inhibit phosphorylation of tyrosine residues in these fusion kinases as well as activation of their downstream signaling targets. Pyrimidylaminobenzamide derivatives are also effective in vitro against an imatinib-resistant T681I mutation in TEL-PDGFRβ. This residue corresponds to T315I in BCR-ABL, a mutation that confers imatinib resistance in patients, which is notoriously difficult to inhibit. Imatinib (International Non-proprietary Name) is a tyrosine kinase inhibitor which is marketed under the designation GLEEVEC® in the US and GLIVEC® in Europe.

It has now been found that pyrimidylaminobenzamide derivatives are useful in the treatment of TEL-PDGFRβ- or FIP1L1-PDGFRα-induced myeloproliferative diseases, especially for the curative and/or prophylactic treatment of myelomonocytic leukaemia, hypereosinophilic syndrome, chronic eosinophilic leukemia and hypereosinophilic syndrome with resistance to imatinib.

SUMMARY OF THE INVENTION

The present invention relates to the use of pyrimidylaminobenzamide compounds of formula (I):

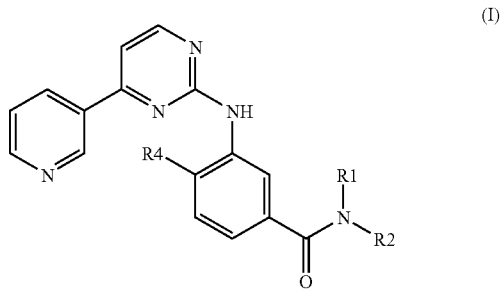

wherein $R_1$ represents hydrogen, lower alkyl, lower alkoxy-lower alkyl, acyloxy-lower alkyl, carboxy-lower alkyl, lower alkoxycarbonyl-lower alkyl, or phenyl-lower alkyl;

$R_2$ represents hydrogen, lower alkyl, optionally substituted by one or more identical or different radicals $R_3$, cycloalkyl, benzcycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or polysubstituted;

and $R_3$ represents hydroxy, lower alkoxy, acyloxy, carboxy, lower alkoxycarbonyl, carbamoyl, N-mono- or N,N-disubstituted carbamoyl, amino, mono- or disubstituted amino, cycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or polysubstituted;

or wherein $R_1$ and $R_2$ together represent alkylene with four, five or six carbon atoms optionally mono- or disubstituted by lower alkyl, cycloalkyl, heterocyclyl, phenyl, hydroxy, lower alkoxy, amino, mono- or disubstituted amino, oxo, pyridyl, pyrazinyl or pyrimidinyl; benzalkylene with four or five carbon atoms; oxaalkylene with one oxygen and three or four carbon atoms; or azaalkylene with one nitrogen and three or four carbon atoms wherein nitrogen is unsubstituted or substituted by lower alkyl, phenyl-lower alkyl, lower alkoxycarbonyl-lower alkyl, carboxy-lower alkyl, carbamoyl-lower alkyl, N-mono- or N,N-disubstituted carbamoyl-lower alkyl, cycloalkyl, lower alkoxycarbonyl, carboxy, phenyl, substituted phenyl, pyridinyl, pyrimidinyl, or pyrazinyl;

$R_4$ represents hydrogen, lower alkyl, or halogen;

and a N-oxide or a pharmaceutically acceptable salt of such a compound for the preparation of a pharmaceutical composition for the treatment of a FIP1L1-PDGFRα or TEL-PDGFRβ-induced myeloproliferative disease, especially for the curative and/or prophylactic treatment of myelomonocytic leukaemia, hypereosinophilic syndrome, chronic eosinophilic leukemia and hypereosinophilic syndrome with resistance to imatinib or myelomonocytic leukemia with resistance to imatinib. The present invention further relates to use of compounds of formula I to treat or prevent myeloproliferative diseases induced by FIP1L1-PDGFRα or TEL-PDGFRβ especially for the curative and/or prophylactic treatment of myelomonocytic leukaemia, chronic eosinophilic leukemia, hypereosinophilic syndrome and hypereosinophilic syndrome with resistance to imatinib.

The general terms used hereinbefore and hereinafter preferably have within the context of this disclosure the following meanings, unless otherwise indicated:

The prefix "lower" denotes a radical having up to and including a maximum of 7, especially up to and including a maximum of 4 carbon atoms, the radicals in question being either linear or branched with single or multiple branching.

Where the plural form is used for compounds, salts, and the like, this is taken to mean also a single compound, salt, or the like.

Any asymmetric carbon atoms may be present in the (R)-, (S)- or (R,S)-configuration, preferably in the (R)- or (S)- configuration. The compounds may thus be present as mixtures of isomers or as pure isomers, preferably as enantiomer-pure diastereomers.

The invention relates also to possible tautomers of the compounds of formula I.

Lower alkyl is preferably alkyl with from and including 1 up to and including 7, preferably from and including 1 to and including 4, and is linear or branched; preferably, lower alkyl is butyl, such as n-butyl, sec-butyl, isobutyl, tert-butyl, propyl, such as n-propyl or isopropyl, ethyl or methyl. Preferably lower alkyl is methyl, propyl or tert-butyl.

Lower acyl is preferably formyl or lower alkylcarbonyl, in particular acetyl.

An aryl group is an aromatic radical which is bound to the molecule via a bond located at an aromatic ring carbon atom of the radical. In a preferred embodiment, aryl is an aromatic radical having 6 to 14 carbon atoms, especially phenyl, naphthyl, tetrahydronaphthyl, fluorenyl or phenanthrenyl, and is unsubstituted or substituted by one or more, preferably up to three, especially one or two substituents, especially selected from amino, mono- or disubstituted amino, halogen, lower alkyl, substituted lower alkyl, lower alkenyl, lower alkynyl, phenyl, hydroxy, etherified or esterified hydroxy, nitro, cyano, carboxy, esterified carboxy, alkanoyl, benzoyl, carbamoyl, N-mono- or N,N-disubstituted carbamoyl, amidino, guanidino, ureido, mercapto, sulfo, lower alkylthio, phenylthio, phenyl-lower alkylthio, lower alkylphenylthio, lower alkylsulfinyl, phenylsulfinyl, phenyl-lower alkylsulfinyl, lower alkylphenylsulfinyl, lower alkylsulfonyl, phenylsulfonyl, phenyl-lower alkylsulfonyl, lower alkylphenylsulfonyl, halogen-lower alkylmercapto, halogen-lower alkylsulfonyl, such as especially trifluoromethanesulfonyl, dihydroxybora (—B(OH)$_2$), heterocyclyl, a mono- or bicyclic heteroaryl group and lower alkylene dioxy bound at adjacent C-atoms of the ring, such as methylene dioxy. Aryl is more preferably phenyl, naphthyl or tetrahydronaphthyl, which in each case is either unsubstituted or independently substituted by one or two substituents selected from the group comprising halogen, especially fluorine, chlorine, or bromine; hydroxy; hydroxy etherified by lower alkyl, e.g. by methyl, by halogen-lower alkyl, e.g. trifluoromethyl, or by phenyl; lower alkylene dioxy bound to two adjacent C-atoms, e.g. methylenedioxy, lower alkyl, e.g. methyl or propyl; halogen-lower alkyl, e.g. trifluoromethyl; hydroxy-lower alkyl, e.g. hydroxymethyl or 2-hydroxy-2-propyl; lower alkoxy-lower alkyl; e.g. methoxymethyl or 2-methoxyethyl; lower alkoxycarbonyl-lower alkyl, e.g. methoxy-carbonylmethyl; lower alkynyl, such as 1-propynyl; esterified carboxy, especially lower alkoxycarbonyl, e.g. methoxycarbonyl, n-propoxy carbonyl or iso-propoxy carbonyl; N-mono-substituted carbamoyl, in particular carbamoyl monosubstituted by lower alkyl, e.g. methyl, n-propyl or iso-propyl; amino; lower alkylamino, e.g. methylamino; di-lower alkylamino, e.g. dimethylamino or diethylamino; lower alkylene-amino, e.g. pyrrolidino or piperidino; lower oxaalkylene-amino, e.g. morpholino, lower azaalkylene-amino, e.g. piperazino, acylamino, e.g. acetylamino or benzoylamino; lower alkylsulfonyl, e.g. methylsulfonyl; sulfamoyl; or phenylsulfonyl.

A cycloalkyl group is preferably cyclopropyl, cyclopentyl, cyclohexyl or cycloheptyl, and may be unsubstituted or substituted by one or more, especially one or two, substitutents selected from the group defined above as substitutents for aryl, most preferably by lower alkyl, such as methyl, lower alkoxy, such as methoxy or ethoxy, or hydroxy, and further by oxo or fused to a benzo ring, such as in benzcyclopentyl or benzcyclohexyl.

Substituted alkyl is alkyl as last defined, especially lower alkyl, preferably methyl; where one or more, especially up to three, substituents may be present, primarily from the group selected from halogen, especially fluorine, amino, N-lower alkylamino, N,N-di-lower alkylamino, N-lower alkanoylamino, hydroxy, cyano, carboxy, lower alkoxycarbonyl, and phenyl-lower alkoxycarbonyl. Trifluoromethyl is especially preferred.

Mono- or disubstituted amino is especially amino substituted by one or two radicals selected independently of one another from lower alkyl, such as methyl; hydroxy-lower alkyl, such as 2-hydroxyethyl; lower alkoxy lower alkyl, such as methoxy ethyl; phenyl-lower alkyl, such as benzyl or 2-phenylethyl; lower alkanoyl, such as acetyl; benzoyl; substituted benzoyl, wherein the phenyl radical is especially substituted by one or more, preferably one or two, substituents selected from nitro, amino, halogen, N-lower alkylamino, N,N-di-lower alkylamino, hydroxy, cyano, carboxy, lower alkoxycarbonyl, lower alkanoyl, and carbamoyl; and phenyl-lower alkoxycarbonyl, wherein the phenyl radical is unsubstituted or especially substituted by one or more, preferably one or two, substituents selected from nitro, amino, halogen, N-lower alkylamino, N,N-di-lower alkylamino, hydroxy, cyano, carboxy, lower alkoxycarbonyl, lower alkanoyl, and carbamoyl; and is preferably N-lower alkylamino, such as N-methylamino, hydroxy-lower alkylamino, such as 2-hydroxyethylamino or 2-hydroxypropyl, lower alkoxy lower alkyl, such as methoxy ethyl, phenyl-lower alkylamino, such as benzylamino, N,N-di-lower alkylamino, N-phenyl-lower alkyl-N-lower alkylamino, N,N-di-lower alkylphenylamino, lower alkanoylamino, such as acetylamino, or a substituent selected from the group comprising benzoylamino and phenyl-lower alkoxycarbonylamino, wherein the phenyl radical in each case is unsubstituted or especially substituted by nitro or amino, or also by halogen, amino, N-lower alkylamino, N,N-di-lower alkylamino, hydroxy, cyano, carboxy, lower alkoxycarbonyl, lower alkanoyl, carbamoyl or aminocarbonylamino. Disubstituted amino is also lower alkylene-amino, e.g. pyrrolidino, 2-oxopyrrolidino or piperidino; lower oxaalkylene-amino, e.g. morpholino, or lower azaalkylene-amino, e.g. piperazino or N-substituted piperazino, such as N-methylpiperazino or N-methoxycarbonylpiperazino.

Halogen is especially fluorine, chlorine, bromine, or iodine, especially fluorine, chlorine, or bromine.

Etherified hydroxy is especially $C_8$-$C_{20}$alkyloxy, such as n-decyloxy, lower alkoxy (preferred), such as methoxy, ethoxy, isopropyloxy, or tert-butyloxy, phenyl-lower alkoxy, such as benzyloxy, phenyloxy, halogen-lower alkoxy, such as trifluoromethoxy, 2,2,2-trifluoroethoxy or 1,1,2,2-tetrafluoroethoxy, or lower alkoxy which is substituted by mono- or bicyclic hetero-aryl comprising one or two nitrogen atoms, preferably lower alkoxy which is substituted by imidazolyl, such as 1H-imidazol-1-yl, pyrrolyl, benzimidazolyl, such as 1-benzimidazolyl, pyridyl, especially 2-, 3- or 4-pyridyl, pyrimidinyl, especially 2-pyrimidinyl, pyrazinyl, isoquinolinyl, especially 3-isoquinolinyl, quinolinyl, indolyl or thiazolyl.

Esterified hydroxy is especially lower alkanoyloxy, benzoyloxy, lower alkoxycarbonyloxy, such as tert-butoxycarbonyloxy, or phenyl-lower alkoxycarbonyloxy, such as benzyloxycarbonyloxy.

Esterified carboxy is especially lower alkoxycarbonyl, such as tert-butoxycarbonyl, iso-propoxycarbonyl, methoxycarbonyl or ethoxycarbonyl, phenyl-lower alkoxycarbonyl, or phenyloxycarbonyl.

Alkanoyl is primarily alkylcarbonyl, especially lower alkanoyl, e.g. acetyl.

N-Mono- or N,N-disubstituted carbamoyl is especially substituted by one or two substituents independently selected from lower alkyl, phenyl-lower alkyl and hydroxy-lower alkyl, or lower alkylene, oxa-lower alkylene or aza-lower alkylene optionally substituted at the terminal nitrogen atom.

A mono- or bicyclic heteroaryl group comprising zero, one, two or three ring nitrogen atoms and zero or one oxygen atom and zero or one sulfur atom, which groups in each case are unsubstituted or mono- or polysubstituted, refers to a heterocyclic moiety that is unsaturated in the ring binding the heteroaryl radical to the rest of the molecule in formula I and is preferably a ring, where in the binding ring, but optionally also in any annealed ring, at least one carbon atom is replaced by a heteroatom selected from the group consisting of nitrogen, oxygen and sulfur; where the binding ring preferably has 5 to 12, more preferably 5 or 6 ring atoms; and which may be unsubstituted or substituted by one or more, especially one or two, substitutents selected from the group defined above as substitutents for aryl, most preferably by lower alkyl, such as methyl, lower alkoxy, such as methoxy or ethoxy, or hydroxy. Preferably the mono- or bicyclic heteroaryl group is selected from 2H-pyrrolyl, pyrrolyl, imidazolyl, benzimidazolyl, pyrazolyl, indazolyl, purinyl, pyridyl, pyrazinyl, pyrimidinyl, pyridazinyl, 4H-quinolizinyl, isoquinolyl, quinolyl, phthalazinyl, naphthyridinyl, quinoxalyl, quinazolinyl, quinnolinyl, pteridinyl, indolizinyl, 3H-indolyl, indolyl, isoindolyl, oxazolyl, isoxazolyl, thiazolyl, isothiazolyl, triazolyl, tetrazolyl, furazanyl, benzo[d]pyrazolyl, thienyl and furanyl. More preferably the mono- or bicyclic heteroaryl group is selected from the group consisting of pyrrolyl, imidazolyl, such as 1H-imidazol-1-yl, benzimidazolyl, such as 1-benzimidazolyl, indazolyl, especially 5-indazolyl, pyridyl, especially 2-, 3- or 4-pyridyl, pyrimidinyl, especially 2-pyrimidinyl, pyrazinyl, isoquinolinyl, especially 3-isoquinolinyl, quinolinyl, especially 4- or 8-quinolinyl, indolyl, especially 3-indolyl, thiazolyl, benzo[d]pyrazolyl, thienyl, and furanyl. In one preferred embodiment of the invention the pyridyl radical is substituted by hydroxy in ortho position to the nitrogen atom and hence exists at least partially in the form of the corresponding tautomer which is pyridin-(1H)2-one. In another preferred embodiment, the pyrimidinyl radical is substituted by hydroxy both in position 2 and 4 and hence exists in several tautomeric forms, e.g. as pyrimidine-(1H, 3H)2,4-dione.

Heterocyclyl is especially a five, six or seven-membered heterocyclic system with one or two heteroatoms selected from the group comprising nitrogen, oxygen, and sulfur, which may be unsaturated or wholly or partly saturated, and is unsubstituted or substituted especially by lower alkyl, such as methyl, phenyl-lower alkyl, such as benzyl, oxo, or heteroaryl, such as 2-piperazinyl; heterocyclyl is especially 2- or 3-pyrrolidinyl, 2-oxo-5-pyrrolidinyl, piperidinyl, N-benzyl-4-piperidinyl, N-lower alkyl-4-piperidinyl, N-lower alkyl-piperazinyl, morpholinyl, e.g. 2- or 3-morpholinyl, 2-oxo-1H-azepin-3-yl, 2-tetrahydrofuranyl, or 2-methyl-1,3-dioxolan-2-yl.

Salts are especially the pharmaceutically acceptable salts of compounds of formula I.

Such salts are formed, for example, as acid addition salts, preferably with organic or inorganic acids, from compounds of formula I with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzene-sulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, a compound of formula I may also form internal salts.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

Compounds within the scope of formula I and the process for their manufacture are disclosed in WO 04/005281 published on Jan. 15, 2004 which is hereby incorporated into the present application by reference. A preferred compound is 4-methyl-3-[[4-(3-pyridinyl)-2-pyrimidinyl]amino]-N-[5-(4-methyl-1H-imidazol-1-yl)-3-(trifluoromethyl)phenyl] benzamide and N-oxides and pharmaceutically acceptable salts thereof of formula (II):

(II)

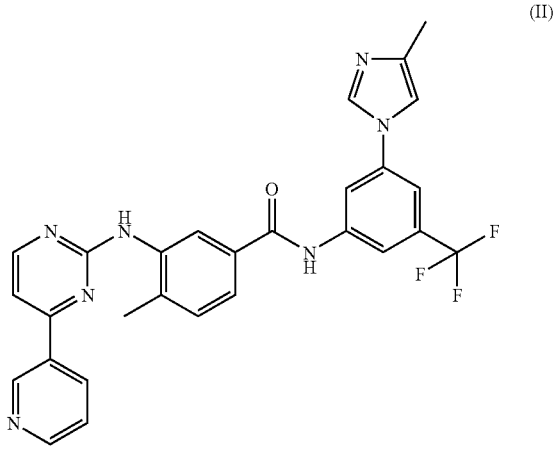

In each case where citations of patent applications or scientific publications are given in particular for compounds of formula (I), the subject-matter of the final products, the pharmaceutical preparations and the claims are hereby incorporated into the present application by reference to these publications.

The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference.

It has now surprisingly been found that compounds of formula (I) possesses therapeutic properties, which render it particularly useful as an inhibitor of PDGFRα (platelet derived growth factor α, also abbreviated as PDGRA) and especially for the treatment and prophylaxis of TEL-PDGFRβ and FIP1L1-PDGFRα-induced diseases such as HES, CEL and HES with resistance to imatinib.

FIP1L1-PDGFRα, as used hereinbefore and hereinafter, is the designation of the fusion product of the genes FIP1L1 (FIP1 like 1) with PDGFRα. TEL-PDGFRβ, as used hereinbefore and hereinafter, is the designation of the fusion product of the genes TEL with PDGFRβ.

Compound (II) inhibited Ba/F3 cells transformed with TEL-PDGFRβ and also effectively inhibited TEL-PDGFRβ tyrosine autophosphorylation, as well as phosphorylation of known PDGFRβ signaling intermediates including PLCγ and PI3K. Compound (II) also inhibited Ba/F3 cells transformed with TEL-PDGFRβ T681I mutant, which is the homologous mutation to T315I mutation in BCR-ABL which confers resistant to imatiniab.

The present invention thus concerns the use of compounds of formula (I) for the preparation of a medicament for the treatment of a FIP1L1-PDGFRα- and TEL-PDGFRβ induced myeloproliferative disease or other disease associated with FIPL1-PDGFRα or TEL-PDGFRβ or similar mutations that activate PDGFR.

The term "a FIP1L1-PDGFRα-induced myeloproliferative disease" as used herein includes, but is not limited to, chronic eosinophilic leukemia, hypereosinophilic syndrome and hypereosinophilic syndrome with resistance to imatinib. This term also specifically includes diseases resulting from FIP1L1-PDGFRα mutation, particularly from the FIP1L1-PDGFRαT674I mutation.

The present invention more particularly concerns the use of compounds of formula (I) for the preparation of a drug for the treatment of myelomonocytic leukaemia, chronic eosinophilic leukemia, CMML hypereosinophilic syndrome, hypereosinophilic syndrome with resistance to imatinib and myelomonocytic leukaemia with resistance to imatinib.

In another embodiment, the instant invention provides a method for treating a FIP1L1-PDGFRα- and TEL-PDGFRβ-induced myeloproliferative disease comprising administering to a mammal in need of such treatment a therapeutically effective amount of compounds of formula (I), or pharmaceutically acceptable salts or prodrugs thereof.

Preferably the instant invention provides a method for treating mammals, especially humans, suffering from a FIP1L1-PDGFRα- or TEL-PDGFRβ-induced myeloproliferative disease comprising administering to a mammal in need of such treatment a FIP1L1-PDGFRα or TEL-PDGFRβ inhibiting amount of 4-Methyl-3-[[4-(3-pyridinyl)-2-pyrimidinyl]amino]-N-[5-(4-methyl-1H-imidazol-1-yl)-3-(trifluoromethyl)phenyl] benzamide (Compound (II)) or a pharmaceutically acceptable salt thereof.

Preferably, this method is used for treating FIP1L1-PDGFRα-induced myeloproliferative diseases.

More preferably, this method is used for treating hypereosinophilic syndrome or hypereosinophilic syndrome with resistance to imatinib.

In another embodiment, the instant invention relates to the use of compounds of formula (I) for the preparation of a pharmaceutical composition for use in treating a FIP1L1-PDGFRα- or TEL-PDGFRβ-induced myeloproliferative disease, more particularly for treating myelomonocytic leukaemia, chronic eosinophilic leukemia, hypereosinophilic syndrome or hypereosinophilic syndrome with resistance to imatinib.

In the present description, the term "treatment" includes both prophylactic or preventative treatment as well as curative or disease suppressive treatment, including treatment of patients at risk of contracting the disease or suspected to have contracted the disease as well as ill patients. This term further includes the treatment for the delay of progression of the disease.

The term "curative" as used herein means efficacy in treating ongoing episodes involving FIP1L1-PDGFRα- or TEL-PDGFRβ-induced myeloproliferative diseases.

The term "prophylactic" means the prevention of the onset or recurrence of diseases involving FIP1L1-PDGFRα- or TEL-PDGFRβ-induced myeloproliferative diseases.

The term "delay of progression" as used herein means administration of the active compound to patients being in a pre-stage or in an early phase of the disease to be treated, in which patients for example a pre-form of the corresponding disease is diagnosed or which patients are in a condition, e.g. during a medical treatment or a condition resulting from an accident, under which it is likely that a corresponding disease will develop.

This unforeseeable range of properties means that the use of compounds of formula (I) are of particular interest for the manufacture of a medicament for the treatment of diseases involving FIP1L1-PDGFRα- or TEL-PDGFRβ-induced myeloproliferative diseases.

This effect can especially be clinically relevant for patients with hypereosinophilic syndrome or hypereosinophilic syndrome with resistance to imatinib.

To demonstrate that compounds of formula (I) are particularly suitable for the treatment of FIP1L1-PDGFRα- or TEL-PDGFRβ-induced myeloproliferative diseases with good therapeutic margin and other advantages, clinical trials can be carried out in a manner known to the skilled person.

The precise dosage of compounds of formula (I) to be employed for inhibiting FIP1L1-PDGFRα or TEL-PDGFRβ activity or for treating FIP1L1-PDGFRα- or TEL-PDGFRβ-induced myeloproliferative diseases depends upon several factors including the host, the nature and the severity of the condition being treated, the mode of administration. The compound of formula I can be administered by any route including orally, parenterally, e.g., intraperitoneally, intravenously, intramuscularly, subcutaneously, intratumorally, or rectally, or enterally. Preferably the compound of formula I is administered orally, preferably at a daily dosage of 1-300 mg/kg body weight or, for most larger primates, a daily dosage of 50-5000, preferably 500-3000 mg. A preferred oral daily dosage is 1-75 mg/kg body weight or, for most larger primates, a daily dosage of 10-2000 mg, administered as a single dose or divided into multiple doses, such as twice daily dosing.

Usually, a small dose is administered initially and the dosage is gradually increased until the optimal dosage for the host under treatment is determined. The upper limit of dosage is that imposed by side effects and can be determined by trial for the host being treated.

Compounds of formula I may be combined with one or more pharmaceutically acceptable carriers and, optionally, one or more other conventional pharmaceutical adjuvants and administered enterally, e.g. orally, in the form of tablets, capsules, caplets, etc. or parenterally, e.g., intraperitoneally or intravenously, in the form of sterile injectable solutions or suspensions. The enteral and parenteral compositions may be prepared by conventional means.

The compounds of formula (I) can be used alone or combined with at least one other pharmaceutically active compound for use in these pathologies. These active compounds can be combined in the same pharmaceutical preparation or in the form of combined preparations "kit of parts" in the sense that the combination partners can be dosed independently or by use of different fixed combinations with distinguished amounts of the combination partners, i.e., simultaneously or at different time points. The parts of the kit of parts can then, e.g., be administered simultaneously or chronologically staggered, that is at different time points and with equal or different time intervals for any part of the kit of parts. Non-limiting examples of compounds which can be cited for use in combination with compounds of formula (I) are cytotoxic chemotherapy drugs, such as cytosine arabinoside, daunorubicin, doxorubicin, cyclophosphamide, VP-16, or imatinib etc. Further, compounds of formula (I) could be combined with other inhibitors of signal transduction or other oncogene-targeted drugs with the expectation that significant synergy would result.

The invention further pertains the combination of a compounds of formula (I) as described hereinbefore with imatinib for the treatment of the diseases and conditions described hereinbefore. The administration of such a combination may be affected at the same time, for instance in the form of a fixed, combined pharmaceutical composition or preparation, or sequentially or timely staggered. The administration of a compounds of formula (I) in a dosage form as described hereinbefore and of imatinib in its marketed form of GLEEVEC® in the US/GLIVEC® in Europe and with the dosages envisaged for these dosage forms is currently preferred.

The treatment of FIP1L1-PDGFRα- or TEL-PDGFRβ-induced myeloproliferative diseases with the above combination may be a so-called first line treatment, i.e. the treatment of a freshly diagnosed disease without any preceeding chemotherapy or the like, or it may also be a so-called second line treatment, i.e. the treatment of the disease after a preceeding treatment with imatrinib or a compounds of formula (I), depending on the severity or stage of the disease as well as the over all condition of the patient etc.

The efficacy of compounds of formula (I) for the treatment of FIP1L1-PDGFRα or TEL-PDGFRβ-induced myeloproliferative diseases is illustrated by the results of the following examples. These examples illustrate the invention without in any way limiting its scope:

Constructs

TEL-PDGFRβ [T/P], FIP1L1-PDGFRα [F/P], and FIP1L1-PDGFRα T6741 cloned in MSCV-IRES-GFP [MSCV-GFP], and TEL-PDGFRβ, TEL-PDGFRβ T681I, and TEL-FGFR3 [T/F] are cloned in MSCV-neomycin [MSCV-neo]. A D842V mutation is introduced into wild-type PDGFRA cDNA and cloned in MSCV-puromycin [MSCV-puro].

Cell Culture, Retrovirus Production, and Transduction of Ba/F3 Cells 293T cells are cultured in Dulbecco's modified Eagle medium (DMEM)+10% fetal bovine serum (FBS). Ba/F3 cells are cultured in RPMI 1640 (RPMI)+10% FBS+1 ng/mL mouse interleukin (IL)-3. Retroviral supernatants are generated and used to transduce Ba/F3 cells. T/P MSCV-neo and T/F MSCV-neo cell lines are selected with 1 mg/mL G418 in the presence of IL-3 for 8-10 days. F/P MSCV-GFP cell lines are selected in RPMI lacking IL-3 for 7-10 days. PDGFRα D842V MSCV-puro cell lines are selected in 2 µg/mL puromycin for 7-14 days. Transformed Ba/F3 cells are grown in RPMI lacking IL-3.

IL-3 Independence Cell Proliferation Assays

The effects of compounds on viability and proliferation of the cells were determined using the luminescent ATP Detection assay kit ATPLite™ from Perkin Elmer Life Sciences (Cat. No: 6016947) according to the instructions of the suppliers. This assay system is based on the production of light (luminescence) caused by the reaction of ATP with added luciferase and D-luciferin.

Ba/F3 FIP-PDGFRα and Ba/F3 Tel-PDGFRβ cell lines, grown in suspension in RPMI 1640 (Invitromex, Cat. No.: L0501), 10% fetal calf serum (Amimed, Cat. No.: 2-01F86-I), 2 mM L-glutamine (Gibco), were seeded into black 96-well tissue culture plates (Packard) at a density of 10000 cells per well in 50 µL complete medium immediately followed by addition of 50 µL per well serial two-fold dilutions of 2× concentrated compounds (duplicates). Cells without compound were used as a control and medium without cells was used to determine the assay background signal. After 70 h incubation (37° C., 5% CO2), the cells were lysed by addition of 50 µL per well mammalian cell lysis solution (provided with the kit) and 5 min shaking in an orbital plate shaker at 700 rpm. Subsequently, 50 µL substrate solution (luciferase and D-luciferin) was added and after 5 min shaking and 10 min dark-adaptation of the plates, light emission was measured with a Packard TopCount.

The compound activity was determined as total growth inhibition (TGI) of the cell cultures and was calculated as follows: After subtraction of the background signal the signal obtained for the control cells was taken as 100%. The effect of the compound was expressed as percent reduction of the control signal. The TGI50 values were determined from the dose response curves by graphical extrapolation.

Compound (II) inhibited the proliferation of both Ba/F3 FIP-PDGFRα and Ba/F3 Tel-PDGFRβ cells with IC50 values of <100 nM.

The T315I mutation in BCR-ABL confers resistance to imatinib and is not inhibited by any known small molecule tyrosine kinase inhibitor. The homologous mutation in TEL-PDGFRβ is T681I, and this mutation also confers imatinib-resistance. Compound (II) inhibited Ba/F3 cells transformed by a TEL-PDGFRβ T681I mutant with an IC50 of <25 nM, similar to that of the non-mutated TEL-PDGFRβ fusion.

Western Blots

For F/P: Ba/F3 cells are incubated with the indicated concentrations of Compound (II) for 4 h in RPMI without FBS or IL-3. Cells are lysed in lysis buffer [PBS with 1M $Na_2EDTA$, 1M NaF, 0.1% Triton X-100, 200 mM $Na_3VO_4$, 200 mM phenylarsine oxide and complete protease inhibitor tablets (Roche)]. 50 µg of protein lysate is combined with reducing SDS loading buffer+dithiothreitol (Cell Signaling) prior to electrophoresis on 10-12% SDS-PAGE gels (Tris-HCL ready-gels, Bio-Rad) and transferred to nitrocellulose membranes. Antibodies used are: phospho-PDGFRα (Tyr 720), PDGFRα 951, Stat5-b (Santa Cruz); phospho-Stat5 (Tyr 694) (Cell Signaling); anti-rabbit peroxidase (Amersham Pharmacia Biotech).

For T/P: Ba/F3 cells stably expressing T/P or T/F are treated with serum starvation in plain RPMI 1640 for 4 hours prior to lysis. The cell extracts are clarified by centrifugation and used for immunoprecipitation or immunoblotting. The enzyme-linked immunoblotting procedures are performed as described. Applied antibodies include: rabbit anti-PDGFRβ serum (Pharmingen); rabbit anti-PI3K (p85) serum; mouse anti-phosphotyrosine 4G10 (Upstate Biotechnology); antibodies against FGFR3, phospho-PI3K p85 (Tyr-508) (Santa Cruz Biotechnology); PLCγ, phospho-PLCγ (Tyr-783) (Cell Signaling).

Bone Marrow Transplants and Drug Treatment of Mice

Murine bone marrow transplant experiments are performed as previously described. MSCV-GFP retroviral supernatants are titered by transducing Ba/F3 cells with supernatant (plus polybrene, 10 µg/mL) and analyzing for the percentage of GFP+ cells by flow cytometry at 48 h post-transduction. Balb/C donor mice (Taconic) are treated for 5-6 days with 5-fluorouracil (150 mg/kg, intraperitoneal injection). Bone marrow cells from donor mice are harvested, treated with red blood cell lysis buffer, and cultured 24 h in transplant medium (RPMI+10% FBS+6 ng/mL IL-3, 10 ng/mL IL-6, and 10 ng/mL stem cell factor). Cells are treated by spin infection with retroviral supernatants (1 mL supernatant per $4 \times 10^6$ cells, plus polybrene) and centrifuged at 2500 rpm for 90 min. 24 h later, the spin infection is repeated, then cells are washed, resuspended in Hank's balanced salt solution, and injected into lateral tail veins of lethally irradiated ($2 \times 450$ rad) Balb/C recipient mice (Taconic) at $0.5-1 \times 10^6$ cells/mouse. Compound (II) is supplied as a powder and prepared as a stock solution in NMP (N-methyl-2-pyrrolidone, Aldrich) and diluted in polyethylene glycol 300 (Sigma) for injections. Starting at day 11 after transplant, animals are treated with 75 mg/kg/day Compound (II) or placebo (polyethylene glycol, identical volume as Compound (II)) every 24 h by oral gavage with 22 gauge gavage needles. Animals are sacrificed when they had palpable splenomegaly or were moribund, or, if healthy, 7 days after sacrifice of the last animal in the placebo group.

Analysis of Myeloproliferative Disease in Mice

Peripheral blood is collected from the retroorbital cavity using heparinized glass capillary tubes and analyzed by automated complete and differential blood cell counts and smears (stained with Wright and Giemsa). Single cell suspensions of spleen and bone marrow are prepared by pressing tissue through a cell strainer, followed by red blood cell lysis. Cells are frozen in 90% FBS, 10% DMSO.

For histopathology, tissues are fixed for at least 72 h in 10% neutral buffered formalin, dehydrated in alcohol, cleared in xylene, and infiltrated with paraffin on an automated processor (Leica). The tissue sections (4 µm) from paraffin-embedded tissue blocks are placed on charged slides and deparaffinized in xylene, rehydrated through graded alcohol solutions, and stained with hematoxylin and eosin.

For flow cytometry, cells are washed in PBS+1% bovine serum albumin (BSA), blocked with Fc-Block (BD Pharmingen) for 10 min on ice, and stained with monoclonal antibodies in PBS+1% BSA for 20 min on ice. Antibodies used are: allophycocyanin (APC)-conjugated Gr1, CD19, and TCRB; and phycoethrin (PE)-conjugated Mac-1, B220, and CD3 (BD Pharmingen). Flow cytometric analysis is performed on a FACSCalibur instrument and analyzed with CellQuest software. Viability is assessed by incubating cells with 7AAD (BD Pharmingen) for 5 min prior to flow cytometry. Cells are gated for viability (using forward/side scatter and 7AAD) and GFP positivity, and 10,000 events are analyzed from this subset for marker expression.

Statistical significance of differences between Compound (II)- and placebo-treated groups in survival time, white blood cell counts, and spleen weights are assessed using a two-sided Mann-Whitney U-test (Wilcoxon rank sum test).

Compound (II) is Effective for Treatment of Myeloproliferative Disease Induced by TEL-PDGFRβ and FIP1L1-PDGFRα in a Murine BMT Assay A murine bone marrow transplant protocol is used to model myeloproliferative disease caused by TEL-PDGFRβ and FIP1L1-PDGFRα. Retroviral transduction of these fusion kinases into bone marrow cells of 5FU-treated donor mice, followed by transplantation into lethally irradiated recipients, produces a rapidly fatal myeloproliferative phenotype characterized by leukocytosis with myeloid predominance, splenomegaly, and extramedullary hematopoiesis.

Donor bone marrow cells are transduced with a murine retroviral vector expressing TEL-PDGFRβ or FIP1L1-PDGFRα and transplanted into recipients. T/P or F/P transplanted mice are divided into two groups that were treated with daily oral gavage of placebo or Compound (II) which was dosed at 150 mg/kg/day, starting at day 11 after transplant.

The TEL-PDGFRβ placebo group developed a completely penetrant myeloproliferative disease with a median latency of 17 days; all T/P treated animals were sacrificed due to disease progression by day 18. In contrast, all animals in the Compound (II)-treated group were still alive at the previously defined study endpoint of 7 days past the time of sacrifice of placebo animals, and there was a statistically significant prolongation of survival in the Compound (II) group (26 days; $p < 0.001$). Compared to placebo treated animals, Compound (II) treated animals also had statistically significant reductions in total white blood cells (WBC) ($563.7 \times 10^6$ cells/mL for placebo vs. $18.6 \times 10^6$ cells/mL for Compound (II), $p < 0.05$) and spleen weight (802.5 mg for placebo vs. 350.0 mg for Compound (II), $p < 0.01$) (Table 1).

TABLE 1

Effects of Compound (II) on characteristics of TEL-PDGFRβ and FIP1L1-PDGFRα-induced myeloproliferative disease

|  | TEL-PDGFRβ Placebo | TEL-PDGFRβ Compound (II) | FIP1L1-PDGFRα Placebo | FIP1L1-PDGFRα Compound (II) |
|---|---|---|---|---|
| WBC (x10$^6$/mL) | | | | |
| Mean | 563.7 | 18.6 | 569.7 | 5.6 |
| Standard deviation | 96.0 | 8.8 | 88.2 | 2.3 |
| Median | 583.4 | 15.9 | 613.2 | 4.7 |
| Range | 459.3-648.3 | 10.9-33.5 | 452.8-659.2 | 4.0-9.6 |
| n | 3 | 5 | 5 | 5 |
| Spleen weight (mg) | | | | |
| Mean | 802.5 | 350.0 | 731.8 | 88.0 |
| Standard deviation | 214.8 | 89.0 | 120.0 | 21.7 |
| Median | 800 | 340 | 700 | 100 |
| Range | 380-1130 | 250-470 | 575-880 | 50-100 |
| n | 8 | 8 | 5 | 5 |
| Liver weight (mg) | | | | |
| Mean | 1746.3 | 1492.5 | 1666.4 | 1128.0 |
| Standard deviation | 546.9 | 103.3 | 135.5 | 90.9 |
| Median | 1910 | 1535 | 1596 | 1090 |
| Range | 590-2410 | 1320-1590 | 1550-1830 | 1080-1290 |
| n | 8 | 8 | 5 | 5 |

Histopathology of hematopoietic organs from placebo mice with TEL-PDGFRβ induced disease demonstrates a massive infiltration of maturing myeloid forms which completely effaced normal splenic architecture. Further examination demonstrates markedly hypercellular bone marrow with a complete predominance of maturing myeloid forms. Extramedullary hematopoiesis is observed in the liver and marked leukocytosis in the peripheral blood. Histopathologic examination of organs from the TEL-PDGFRβ Compound (II)-treated mice show a significantly less severe myeloproliferative disease than their placebo-treated counterparts, though features of myeloid expansion are still present. While splenic architecture of the TEL-PDFGRβ Compound (II)-treated animals is perturbed, there is a relative preservation of splenic red and white pulp in comparison with spleens from the placebo-treated group. Further analysis of spleens from Compound (II)-treated animals also demonstrates that splenic red pulp appear to be expanded by an admixture of both maturing myeloid forms and erythroid elements in contrast to the predominantly myeloid population observed in placebo-treated animals. Similar changes are also noted in the bone marrow of Compound (II)-treated animals which, despite being hypercellular, display an admixture of both myeloid and erythroid elements versus the completely myeloid predominant bone marrows of the placebo treated group. Finally, the significantly reduced tumor burden of TEL-PDGFRβ Compound (II) treated animals is also reflected in liver sections from these animals which display only focal patches of extramedullary hematopoiesis compared to the extensive liver involvement observed in the placebo-treated animals.

FACS analysis of spleen of T/P placebo animals show a marked increase in Gr1+/Mac1+ cells and a decrease in B lymphoid cells (B220+, CD19+) compared to normal spleen. In corroboration with the histopathological findings, Compound (II)-treated animals show a similar pattern of myeloproliferation, but with a consistently reduced percentage of Gr1+/Mac1+ cells and a slightly increased percentage of B220+/CD19+ compared to the placebo group.

In the FIP1L1-PDGFRα bone marrow transplant experiment, more differences between placebo and Compound (II) groups are observed. Placebo-treated animals rapidly develop a fatal myeloproliferative disease similar to that previously described for FIP1L1-PDGFRα. Whereas all placebo animals are lost to disease by day 24, all Compound (II)-treated animals remained alive and healthy until day 33 when the study was terminated. Compared to placebo, Compound (II) treatment was correlated with significant reductions in total WBC (569.7×10$^6$ cells/mL for placebo vs. 5.6×10$^6$ cells/mL for Compound (II), $p<0.01$) and spleen weight (731.8 mg for placebo vs. 88.0 mg for Compound (II), $p<0.01$) (Table 1).

Histopathologic and FACS analysis revealed evidence of severe myeloproliferative disease in FIP1L1-PDGFRα placebo-treated animals, as demonstrated by a massive infiltration of maturing myeloid elements in the spleens and bone marrows, as well as extensive degrees of extramedullary hematopoiesis in the livers of the placebo-treated group. In contrast, examination of hematopoietic organs from Compound (II)-treated animals display a striking preservation of normal splenic architecture with substantially reduced amounts of maturing myeloid elements in the red pulp which was corroborated by flow cytometric analyses of splenocytes derived from these animals. Bone marrow sections from drug-treated animals also showed dramatic improvement over placebo-treated animals and were less cellular with the reappearance of fat spaces and more normal ratios of myeloid to erythroid elements. Finally, the efficacy of Compound (II) in these drug-treated animals was demonstrated by the notable absence of any extramedullary hematopoiesis in their livers.

Clinical Study

The effect of Compound (II) on FIP1L1-PDGFR-α transcript levels and mutation status of c-kit/PDGFR-a in malignant cells taken from the blood and/or bone marrow is assessed. HES, SM and CEL may result from a novel fusion kinase: FIP1L1-PDGFR-α SM may also result from an activating mutation in the KIT gene. Q-RT-PCR for FIP1L1-PDGFR-α transcript at Baseline, cycle 1 day 15, cycle 1, 2, 3 day 28 and every 3rd subsequent cycle, end of study. Mutation analysis of c-kit, PDGFR-a. Three separate groups, each with the following patient populations: HES/CEL Endpoints: response rates after 3 months of therapy.

The invention claimed is:

1. A method of treating hypereosinophilic syndrome in a patient in need thereof comprising administering to the patient an effective amount of 4-Methyl-3-[[4-(3-pyridinyl)-2-pyrimidinyl]amino]-N-[5-(4-methyl-1-H-imidazol-1-yl)-3-(trifluoromethyl)phenyl] benzamide of formula (II):

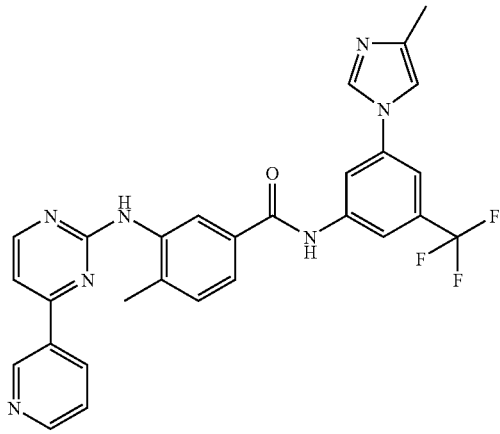

or pharmaceutically acceptable salts thereof.

2. A method according to claim 1, wherein the hypereosinophilic syndrome is resistant to treatment with imatinib.

3. A method of treating hypereosinophilic syndrome in a patient in need thereof comprising administering to the patient a pharmaceutical composition comprising a pharmaceutical carrier and an effective amount of a compound of formula (II):

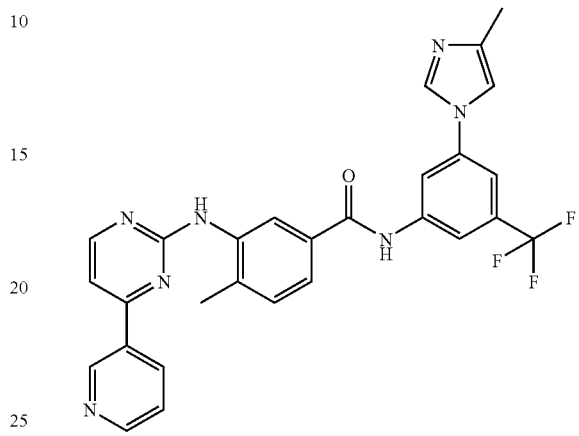

or pharmaceutically acceptable salts thereof.

4. A method according to claim 3, wherein the hypereosinophilic syndrome is resistant to treatment with imatinib.

* * * * *